(12) United States Patent
Beck et al.

(10) Patent No.: US 11,730,601 B2
(45) Date of Patent: Aug. 22, 2023

(54) CUSTOMIZED PATIENT-SPECIFIC 3D PRINTED POSITIONING AUGMENT FOR ORTHOPAEDIC SURGICAL IMPLANT

(71) Applicant: DePuy Synthes Products, Inc., Raynham, MA (US)

(72) Inventors: Clinton A. Beck, Fort Wayne, IN (US); Jeffrey R. Roose, Milford, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 438 days.

(21) Appl. No.: 16/856,393

(22) Filed: Apr. 23, 2020

(65) Prior Publication Data

US 2021/0330463 A1 Oct. 28, 2021

(51) Int. Cl.
| A61F 2/34 | (2006.01) |
| A61F 2/30 | (2006.01) |
| G06T 7/149 | (2017.01) |
| G06T 7/00 | (2017.01) |

(52) U.S. Cl.
CPC ............ *A61F 2/30942* (2013.01); *A61F 2/34* (2013.01); *G06T 7/0012* (2013.01); *G06T 7/149* (2017.01); *A61F 2002/3097* (2013.01); *A61F 2002/30957* (2013.01); *A61F 2002/30968* (2013.01); *A61F 2002/30985* (2013.01); *A61F 2240/004* (2013.01); *G06T 2207/30008* (2013.01); *G06T 2207/30052* (2013.01)

(58) Field of Classification Search
CPC ............... A61F 2/34; A61F 2/30942; A61F 2002/30736
See application file for complete search history.

(56) References Cited

U.S. PATENT DOCUMENTS

| 5,879,404 A | * | 3/1999 | Bateman | A61F 2/34 |
| | | | | 623/22.21 |
| 8,568,487 B2 | | 10/2013 | Witt et al. | |
| 2011/0087332 A1 | * | 4/2011 | Bojarski | A61B 17/1764 |
| | | | | 623/20.32 |
| 2013/0053968 A1 | * | 2/2013 | Nardini | A61F 2/4081 |
| | | | | 623/19.11 |
| 2018/0185168 A1 | | 7/2018 | Kelman et al. | |
| 2018/0344465 A1 | | 12/2018 | McPherson et al. | |
| 2019/0076256 A1 | | 3/2019 | Macke | |

FOREIGN PATENT DOCUMENTS

| CN | 108904104 A | 11/2018 |
| WO | 2017098039 A1 | 6/2017 |

OTHER PUBLICATIONS

International Search Report for International Appln. No. PCT/IB2021/053083, dated Jun. 22, 2021, 7 pages.

\* cited by examiner

*Primary Examiner* — Brian A Dukert
(74) *Attorney, Agent, or Firm* — Barnes & Thornburg LLP

(57) ABSTRACT

An orthopaedic prosthetic component includes a manufactured acetabular shell component having an outer wall and an additively manufactured augment coupled to the outer wall. The augment includes an outer surface that defines a customized patient-specific negative contour shaped to conform to a positive contour of a patient's bone. A method for manufacturing the prosthetic component is also disclosed.

16 Claims, 4 Drawing Sheets

CUSTOMIZED PATIENT-SPECIFIC 3D PRINTED POSITIONING AUGMENT FOR ORTHOPAEDIC SURGICAL IMPLANT

TECHNICAL FIELD

The present disclosure relates generally to orthopaedic surgical implants and, more particularly, to customized patient-specific orthopaedic surgical implants.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

Accurate positioning of the acetabular cup is an important factor in achieving function and longevity of the prosthetic hip joint. The consequences of malposition may include instability, increased wear, impaired muscle function, reduced range of motion (ROM), impingement, bearing-related noise generation, poor functional outcomes, limb length discrepancy, and loosening and cup failure.

To facilitate the replacement of the natural joint with a prosthesis, orthopaedic surgeons use a variety of orthopaedic surgical instruments such as, for example, cutting blocks, drill guides, milling guides, alignment guides and other surgical instruments. Typically, the orthopaedic surgical instruments are reusable and generic with respect to the patient such that the same orthopaedic surgical instrument may be used on a number of different patients during similar orthopaedic surgical procedures. The orthopaedic surgical instruments may also be customized to a specific patient. Such "customized patient-specific orthopaedic surgical instruments" are single-use surgical tools for use by a surgeon in performing an orthopaedic surgical procedure that is intended, and configured, for use on a particular patient.

SUMMARY

According to one aspect of the disclosure, a method for manufacturing an orthopaedic prosthetic includes providing a manufactured acetabular shell component having an outer wall; and additively manufacturing an augment coupled to the outer wall of the manufactured acetabular shell component, wherein the augment comprises an outer surface that defines a customized patient-specific negative contour shaped to conform to a positive contour of a patient's bone. In an embodiment, the augment includes an additively manufactured metallic component.

In an embodiment, the method further includes determining a target orientation of the manufactured acetabular shell component relative to a position of the positive contour of the patient's bone; and determining a position of the augment on the outer wall of the manufactured acetabular shell component based on the target orientation.

In an embodiment, the method further includes identifying the positive contour of the patient's bone based on one or more medical images of the patient's bone. In an embodiment, identifying the positive contour may include generating a three-dimensional model of the patient's bone based on the one or more medical images of the patient's bone. In an embodiment, the method further includes capturing the one or more medical images of the patient's bone, wherein identifying the positive contour comprises identifying the positive contour in response to capturing the one or more medical images.

In an embodiment, the outer wall of the manufactured acetabular shell component includes a distal rim and an outer surface that extends from the distal rim, and wherein the augment extends outwardly from the outer surface at a position adjacent to the distal rim.

In an embodiment, the positive contour of the patient's bone includes a bony landmark of the patient's bony geometry. In an embodiment, the positive contour includes a transverse acetabular ligament landmark. In an embodiment, the positive contour of the patient's bone defines a void in the patient's bony geometry.

According to another aspect, an orthopaedic prosthetic component includes a manufactured acetabular shell component having an outer wall; and an additively manufactured augment coupled to the outer wall of the manufactured acetabular shell component, wherein the augment comprises an outer surface that defines a customized patient-specific negative contour shaped to conform to a positive contour of a patient's bone.

In an embodiment, the manufactured acetabular shell component includes a distal rim that defines a component axis; and the augment is located at a position on the outer wall of the manufactured acetabular shell component that fixes an orientation of the component axis relative to a position of the positive contour of the patient's bone.

In an embodiment, the augment includes a porous outer surface. In an embodiment, the manufactured acetabular shell component includes a porous coating coupled to the outer wall, and wherein the augment is coupled to the porous coating.

In an embodiment, the outer wall of the manufactured acetabular shell component includes a distal rim and an outer surface that extends from the distal rim, and wherein the augment extends outwardly from the outer surface at a position adjacent to the distal rim.

In an embodiment, the positive contour of the patient's bone includes a bony landmark of the patient's bony geometry. In an embodiment, the positive contour includes a transverse acetabular ligament landmark. In an embodiment, the positive contour of the patient's bone defines a void in the patient's bony geometry.

In an embodiment, the manufactured acetabular shell component includes a forged metallic component or a machined metallic component. In an embodiment, the augment includes an additively manufactured metallic component.

BRIEF DESCRIPTION OF THE DRAWINGS

The detailed description particularly refers to the following figures, in which.

DETAILED DESCRIPTION OF THE DRAWINGS

Figure 1:
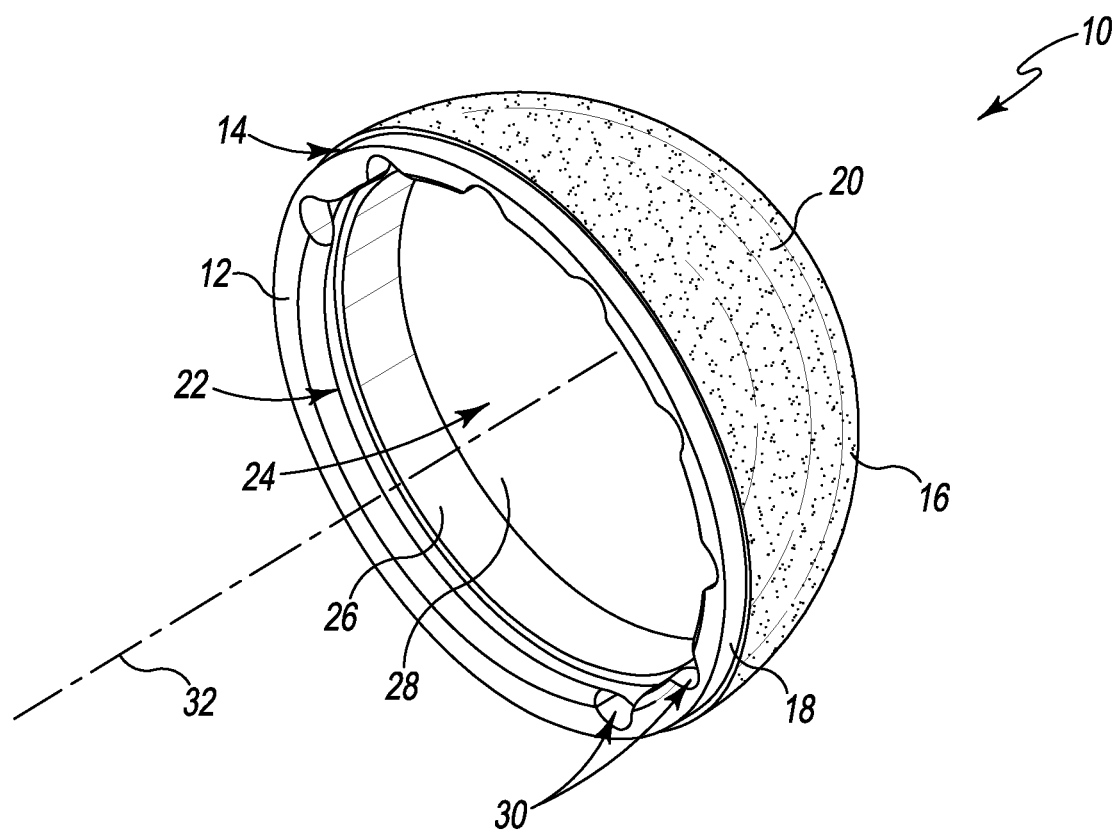
FIG. 1 is a perspective view of an prosthetic acetabular shell component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an illustrative acetabular prosthetic shell component 10 is shaped to be implanted in a surgically-prepared acetabulum of a patient's pelvis. The shell component 10 is conventionally manufactured from an implant-grade metallic material such as cobalt chromium or titanium. For example, in some embodiments, the shell component 10 may be forged and/or machined. The shell component 10 may be a standard, non-patient-specific implant or prostheses that has a standard size and shape (and/or is selected from a group of standard implant sizes and/or shapes).

The shell component 10 has a distal rim 12 and an outer wall 14 that extends from the distal rim 12. The outer wall 14 includes a convex curved outer surface 16 and an annular outer surface 18 that extends from the distal rim 12 to the curved outer surface 16. In the illustrative embodiment, the convex curved outer surface 16 is semi-spherical and shaped to match the shape of a patient's surgical prepared acetabulum. The shell component 10 also includes a Porocoat® outer coating 20 that permits bone to affix biologically to the shell component 10 after implantation. The Porocoat® outer coating 20 covers the outer surface 16 and follows its geometric shape. It should be appreciated that in other embodiments the Porocoat® outer coating 20 may be omitted.

The shell component 10 further includes an inner wall 22 that extends inwardly from the distal rim 12 to define a cavity 24 in the shell component 10. The illustrative cavity 24 is sized to receive a shell liner component (not shown), which may be formed from a polymeric material such as, for example, polyethylene, a ceramic material, a metallic material, or other material. The inner wall 22 of the shell component 10 includes an annular inner surface 26 that is positioned opposite the annular outer surface 18, and a concave curved inner surface 28 that is opposite the convex curved outer surface 16. A plurality of slots 30 extend outwardly from the inner wall 22 of the distal rim 12. The slots 30 are spaced apart around the circumference of the distal rim 12 and are shaped to receive corresponding keys of the shell liner component and/or other prosthetic component. The distal rim 12 defines an axis 32 extending through the cavity 24. In some embodiments, one or more slots or other fixation guides may be defined through the curved surfaces 16, 28. In use, screws, pins, or other fasteners may be inserted through the fixation guides to secure the shell component to the patient's bone.

As described further below, the shell component 10 may be used with an additive manufacturing process to attach one or more patient-specific augments to the outer wall 14 to generate an augmented shell component 10' (see FIG. 3). The augmented shell component 10' may be implanted into a patient's hip during an orthopaedic surgical procedure such as total hip arthroplasty.

Figure 2:
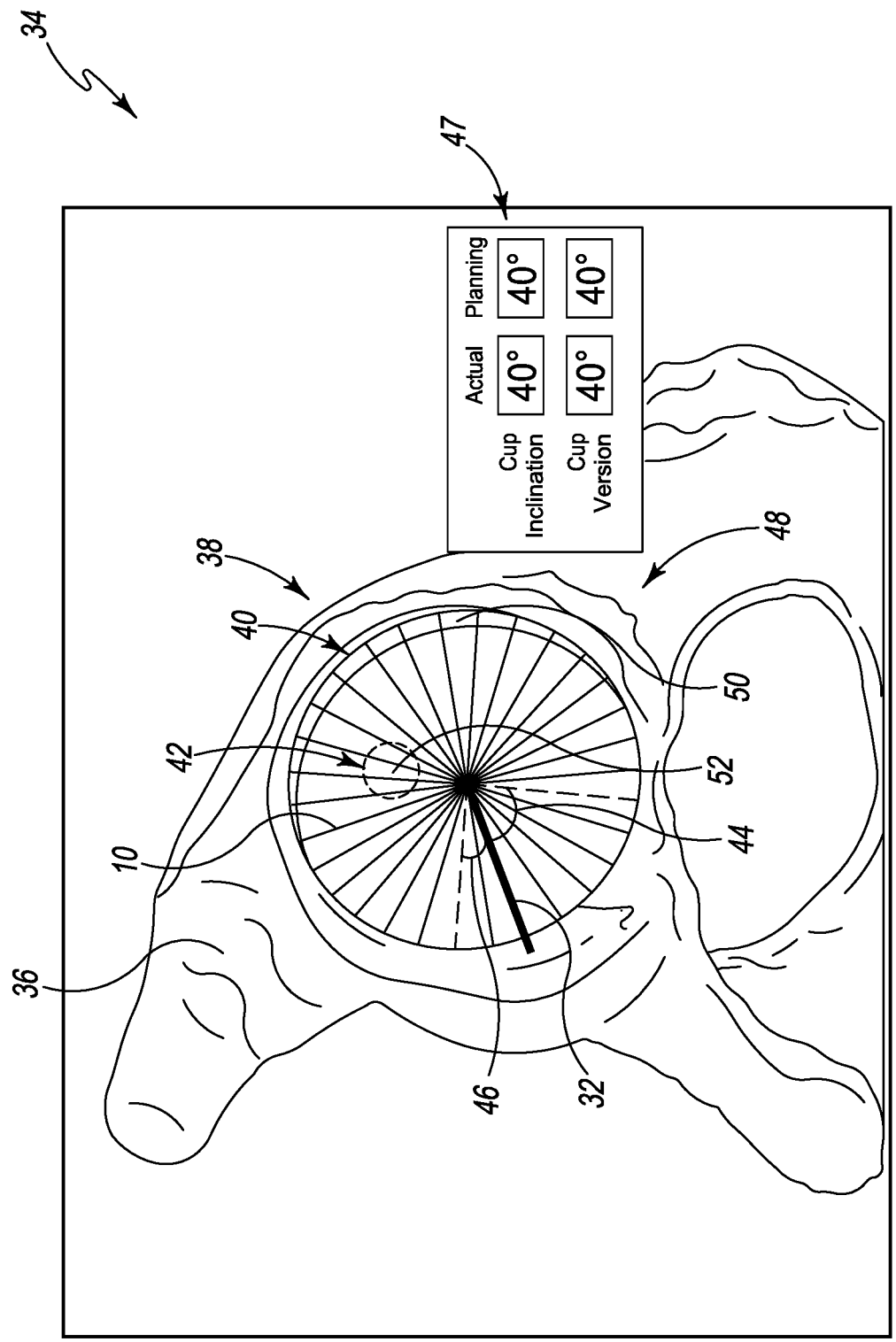
FIG. 2 is a schematic illustration of a pre-operative planning tool for an orthopaedic surgical procedure.

Referring now to FIG. 2, a pre-operative planning interface 34 for the orthopaedic surgical procedure is shown. Prior to surgery, a three-dimensional model 36 of a patient's pelvis is developed based on imaging of the patient's pelvis. To generate the three dimensional model 36, a number of medical images of the relevant bony anatomy or joint of the patient are generated. To do so, the orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's joint. Additionally or alternatively, the medical images may be embodied as any number of computed tomography (CT) images, magnetic resonance imaging (MRI) images, or other three-dimensional medical images.

After generating or otherwise receiving the medical images, a three-dimensional model 36 of the patient's pelvis is generated based on the medical images. In particular, a computing device or other modeling system may perform an x-ray segmentation process to model the patient's bone based on the input x-ray images. As shown in FIG. 2, the illustrative three-dimensional model 36 includes contours and other surface geometry of the patient's acetabulum 38, including bony landmarks such as the transverse acetabular ligament (TAL) or other bony features. For example, the illustrative model 36 includes a contour 40 of the rim of the acetabulum 38. The model 36 further includes a contour 42 of a void in an inner wall of the acetabulum 38.

As shown, the interface 34 further includes a representation of the shell component 10, including a representation of the axis 32. Using the interface 34, the orthopaedic surgeon or other user may determine a target orientation of the shell component 10 (including the axis 32) in relation to the model 36. This orientation relative to the model 36 corresponds to a desired position and orientation for the shell component 10 relative to the patient's bony geometry. For example, as shown in FIG. 2, the surgeon or other user may adjust an inclination angle 44 and a version angle 46 in order to orient the axis 32 of the shell component 10 relative to the model 36. In other embodiments, the surgeon or other user may adjust any other angle that defines the orientation of the shell component 10. In some embodiments, orientation of the shell component 10 may be determined automatically, for example to achieve a predetermined inclination angle 44 and/or a predetermined version angle 46 (e.g., between 40-45 degrees inclination and between 15-20 degrees anteversion). In some embodiments, the interface 34 may include a control 47 that allows the surgeon or other user to view and/or adjust the angles 44, 46.

After determining the target orientation of the shell component 10, the surgeon or other operator positions one or more personalized geometry features 48 on the shell component 10. Additionally or alternatively, the personalized geometry features 48 may be generated and/or positioned automatically relative to the shell component 10. As described further below, the personalized geometry features 48 each include one or more negative contours that match and receive a corresponding positive contour of the patient's bony geometry that is captured in the model 36. Because each personalized geometry feature 48 matches a particular landmark or other positive contour of the model 36, the position and orientation of the personalized geometry features 48 relative to the model 36 are fixed. Accordingly, when the shell component 10 is in a particular orientation relative to the model 36, the position and orientation of each of the personalized geometry features 48 is also fixed relative to the shell component 10.

For example, in the illustrative embodiment, a personalized geometry feature 50 matches the contour 40 of the acetabular rim. The feature 50 thus includes one or more contours that are negatives of the positive contour 40. The geometry feature 50 is positioned near the distal rim 12, on a part of the convex outer surface 16 of the shell component 10 that, when the shell component 10 is positioned in the target orientation, is exposed above the acetabulum 38. In another example, a personalized geometry feature 52 matches the void contour 42. Similarly, the feature 52 includes one or more contours that are negatives of the positive contour 42. The geometry feature 52 is positioned on the convex outer surface 16 at a position that, when the shell component 10 is positioned in the target orientation, is aligned with the void in the wall of the acetabulum 38.

After determining the negative contour, the position, and the orientation of each of the personalized geometry features 48, the personalized geometry features 48 are used with an additive manufacturing process to generate a patient-specific augmented shell component 10'. The additive manufacturing process starts with a conventionally manufactured shell component 10 as described above. The shell component 10 may be a metallic component that is forged, machined, or otherwise conventionally manufactured. During the additive manufacturing process, one or more patient-specific augments 54 are attached to the outer wall 14 of the shell component 10, producing the augmented shell component 10'.

Figure 3:
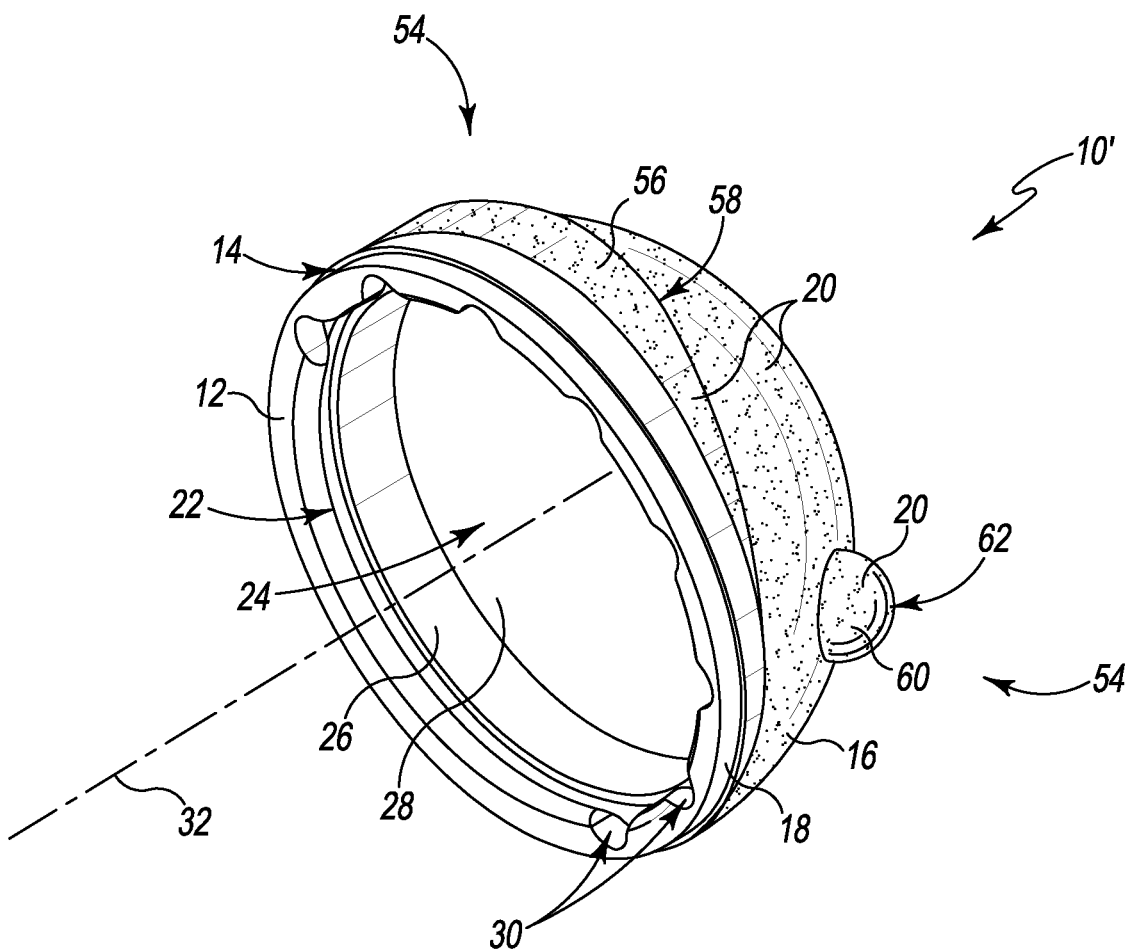
FIG. 3 is a perspective view of the prosthetic acetabular shell component of FIG. 1 including positioning augments.

Referring now to FIG. 3, the shell component 10' is shown after the additive manufacturing process. Each of the augments 54 is formed from a metallic material deposited on the outer wall 14 of the shell component 10 using one or more forms of additive manufacturing technology such as, for example, Selective Laser Sintering (SLS), Direct Metal Laser Sintering (DMLS), 3D printing, or other additive manufacturing technology. The augments 54 also include a porous coating 20 or in some embodiments may be entirely porous.

Each augment 54 includes an outer surface having a negative contour that matches a positive contour of the patient's bony geometry determined during preoperative planning as described above. For example, each augment 54 may be generated using one or more three-dimensional models or other data describing the personalized geometry features 48 determined during the pre-operative planning process described above.

The illustrative shell component 10' includes an augment 56 positioned on the outer surface 16 adjacent to the distal rim 12 as well as an augment 60 positioned on the convex outer surface 16. The augment 56 is an off-axis step that includes an outer surface 58, and illustratively has the shape of the personalized geometry feature 50 described above. Thus, the outer surface 58 defines a negative contour that matches the positive contour 40 of the patient's acetabular rim as described above in connection with the pre-operative planning procedure.

Similarly, the augment 60 is a void filler that has the shape of the personalized geometry feature 52 described above. Thus, the augment 60 includes an outer surface 62 that defines a negative contour that matches the positive contour 42 of the void in the patient's acetabulum as described above in connection with the pre-operative planning procedure.

Therefore, the illustrative shell component 10' including the augments 54 is configured to engage the patient's acetabulum 38 at a unique predetermined location and orientation. Of course, in other embodiments the shell component 10' may include a different number and/or arrangements of augments 54. In each embodiment, each augment 54 includes a patient-specific negative contour that matches a positive contour of the patient's bony geometry determined during pre-operative planning.

After the additive manufacturing process is completed, the shell component 10' is thus a customized patient-specific orthopaedic implant. What is meant herein by the term "customized patient-specific orthopaedic implant" is a surgical implant or prosthesis for use by a surgeon in performing an orthopaedic surgical procedure that is intended, and configured, for use on a particular patient. As such, it should be appreciated that, as used herein, the term "customized patient-specific orthopaedic surgical implant" is distinct from standard, non-patient-specific orthopaedic surgical implants that are not fabricated or customized to any particular patient.

Figure 4:
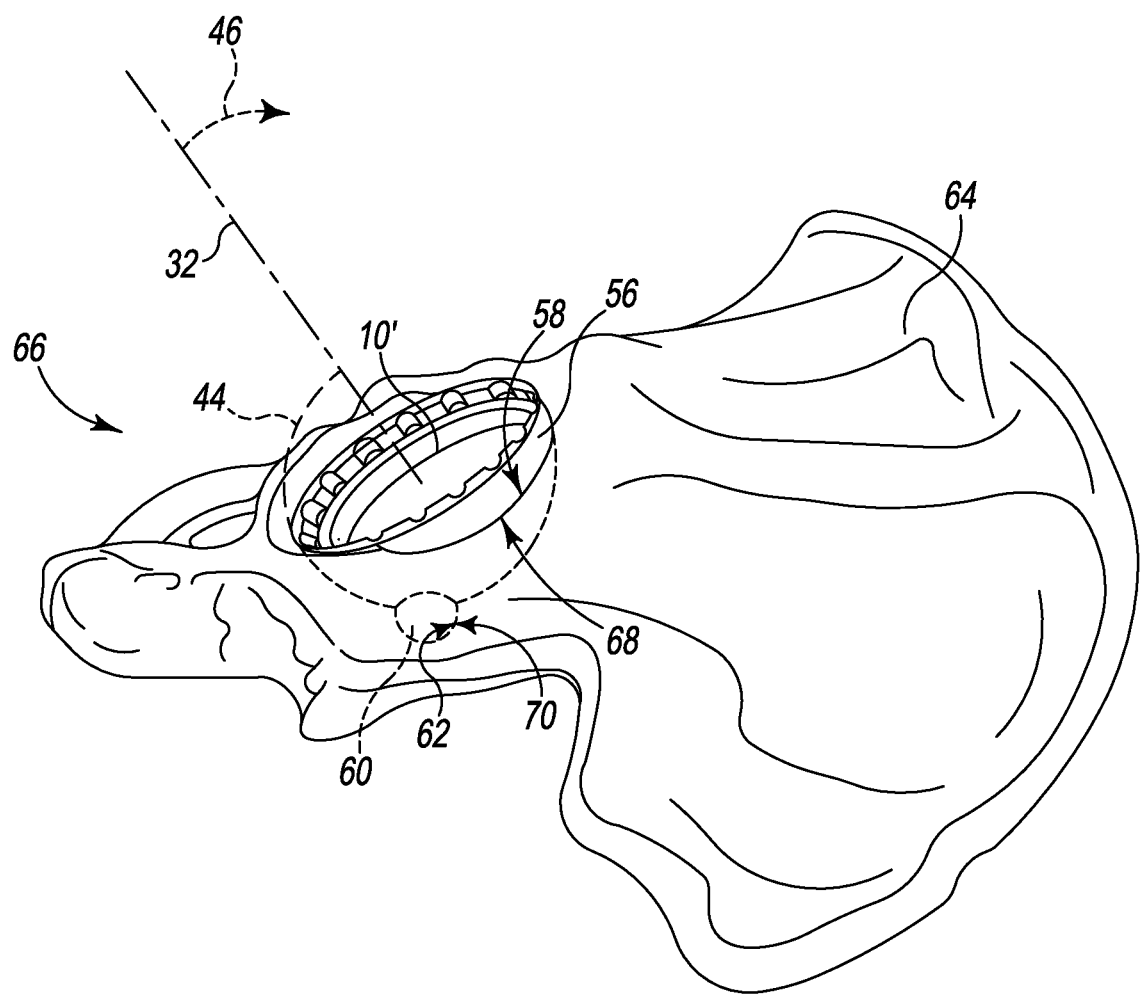
FIG. 4 is a perspective view showing the acetabular shell component of FIG. 3 installed in a patient's hip.

Referring now to FIG. 4, during use, the orthopaedic surgeon inserts the shell component 10' including the augments 54 into the patient's pelvis 64. First, the surgeon surgically prepares the patient's bone to receive the shell component 10'. To do so, the surgeon may utilize a surgical reamer to prepare the patient's acetabulum 66 to receive the shell component 10'.

The surgeon next inserts the shell component 10' into the patient's surgically prepared acetabulum 66 using the augments 54 as a positioning guide for the shell component 10'. When inserted, negative contours of the 3D printed augments 54 of the shell component 10' match and receive corresponding positive contours of the patient's bony anatomy. For example, in the illustrative embodiment, the outer surface 58 of the off-axis step 56 matches an acetabular rim contour 68, which corresponds to the contour 40 of the model 36. Similarly, the outer surface 62 of the void filler 60 matches a void contour 70, which corresponds to the contour 42 of the model 36. As described above, those contours are determined during pre-operative planning, for example using the pre-operative interface 34.

As shown in FIG. 4, when the shell component 10' is inserted in the surgically prepared acetabulum 66 such that the augments 54 match corresponding contours of the patient's bony anatomy, the shell component 10' is positioned in a particular predetermined orientation relative to the patient's pelvis 64. The orientation of the shell component 10' matches the target orientation determined using the pre-operative planning interface 34. In particular, as illustrated by the axis 32, the shell component 10' is oriented at the target inclination angle 44 and the target version angle 46.

After positioning the shell component 10' in the surgically prepared acetabulum 66, the shell component 10' is impacted, cemented, or otherwise fixed in the predetermined position and orientation. Thus, the shell component 10' including augments 54 as described herein may allow for insertion of the shell component at a predetermined orientation (e.g., inclination and version) without the use of additional alignment guides, shell trials, or other surgical instruments. Accordingly, the shell component 10' with augments 54 may reduce cost, reduce operation time, and increase positioning accuracy for inserting the shell component 10'. Further, by 3D printing the augments 54 onto a conventionally manufactured shell component 10, the shell component 10' may reduce costs and/or improve strength as compared to fully 3D printed components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. A method for manufacturing an orthopaedic prosthetic, the method comprising:
   providing a manufactured acetabular shell component having an outer wall, wherein the outer wall comprises a distal rim and an outer surface that extends from the distal rim;
   receiving a specified inclination angle or a specified version angle for the manufactured acetabular shell component;
   determining a target orientation of the manufactured acetabular shell component relative to a patient's bone as a function of the specified inclination angle or the specified version angle, the target orientation defining an inclination angle corresponding to the specified inclination angle or a version angle corresponding to the specified version angle;
   determining a position of an augment on the outer wall of the manufactured acetabular shell component, the position corresponding to a positive contour of the patient's bone when the manufactured acetabular shell component is positioned in the target orientation; and
   additively manufacturing the augment coupled to the outer wall of the manufactured acetabular shell component at the position on the outer wall, wherein the augment extends outwardly from the outer surface at a position adjacent to the distal rim, wherein the augment comprises an outer surface that defines a customized patient-specific negative contour shaped to conform to the positive contour of a patient's bone, and wherein the positive contour comprises an acetabular rim of the patient's bone.

2. The method of claim 1, further comprising identifying the positive contour of the patient's bone based on one or more medical images of the patient's bone.

3. The method of claim 2, wherein identifying the positive contour comprises generating a three-dimensional model of the patient's bone based on the one or more medical images of the patient's bone.

4. The method of claim 2, further comprising capturing the one or more medical images of the patient's bone, wherein identifying the positive contour comprises identifying the positive contour in response to capturing the one or more medical images.

5. The method of claim 1, wherein the positive contour of the patient's bone comprises a bony landmark of the patient's bony geometry.

6. The method of claim 5, wherein the positive contour comprises a transverse acetabular ligament landmark.

7. The method of claim 1, wherein the positive contour of the patient's bone defines a void in the patient's bony geometry.

8. The method of claim 1, wherein the augment comprises an additively manufactured metallic component.

9. An orthopaedic prosthetic component comprising:
   a manufactured acetabular shell component having an outer wall; and
   an additively manufactured augment coupled to the outer wall of the manufactured acetabular shell component, wherein the augment comprises an outer surface that defines a customized patient-specific negative contour shaped to conform to a positive contour of a patient's bone;
   wherein the outer wall of the manufactured acetabular shell component comprises a distal rim and an outer surface that extends from the distal rim, and wherein the augment extends outwardly from the outer surface at a position adjacent to the distal rim; and
   wherein the positive contour of the patient's bone comprises an acetabular rim of the patient's bone;
   wherein the distal rim defines a component axis, the position of the augment fixes an orientation of the component axis relative to the positive contour of the patient's bone, and the orientation defines an inclination angle that corresponds to a predetermined inclination angle or a version angle that corresponds to a predetermined version angle.

10. The orthopaedic prosthetic component of claim 9, wherein the augment comprises a porous outer surface.

11. The orthopaedic prosthetic component of claim 10, wherein the manufactured acetabular shell component comprises a porous coating coupled to the outer wall, and wherein the augment is coupled to the porous coating.

12. The orthopaedic prosthetic component of claim 9, wherein the positive contour of the patient's bone comprises a bony landmark of the patient's bony geometry.

13. The orthopaedic prosthetic component of claim 12, wherein the positive contour comprises a transverse acetabular ligament landmark.

14. The orthopaedic prosthetic component of claim 9, wherein the positive contour of the patient's bone defines a void in the patient's bony geometry.

15. The orthopaedic prosthetic component of claim 9, wherein the manufactured acetabular shell component comprises a forged metallic component or a machined metallic component.

16. The orthopaedic prosthetic component of claim 9, wherein the augment comprises an additively manufactured metallic component.

\* \* \* \* \*